United States Patent [19]

Heim

[11] 4,090,078
[45] May 16, 1978

[54] METHOD AND ARRANGEMENT FOR DETERMINING ALCOHOL CONTENT IN THE BREATH

[75] Inventor: Ulrich Heim, Reinfeld, Germany

[73] Assignee: Dragerwerk Aktiengesellschaft, Germany

[21] Appl. No.: 762,807

[22] Filed: Jan. 26, 1977

[30] Foreign Application Priority Data

Mar. 13, 1976 Germany .............................. 2610578

[51] Int. Cl.² ........................................... G01N 21/26
[52] U.S. Cl. ................................. 250/343; 23/232 E; 23/254 E; 73/23; 128/2 C
[58] Field of Search ............. 23/232 R, 232 E, 254 R, 23/254 E; 128/2 C, 2.08; 250/343, 338; 73/23, 421.5 R

[56] References Cited

U.S. PATENT DOCUMENTS

| | | | |
|---|---|---|---|
| 2,867,511 | 1/1959 | Harger | 23/254 R |
| 3,622,278 | 11/1971 | Elzinga et al. | 23/232 R |
| 3,726,270 | 4/1973 | Griffis et al. | 23/254 E X |
| 3,823,601 | 7/1974 | Hoppesch | 23/254 E X |
| 3,830,630 | 8/1974 | Kiefer et al. | 23/232 E |
| 3,842,345 | 10/1974 | Padgitt et al. | 23/232 E X |
| 3,910,261 | 10/1975 | Ragsdale et al. | 23/254 R X |
| 3,951,607 | 4/1976 | Fraser | 23/254 E |

*Primary Examiner*—Joseph Scovronek
*Attorney, Agent, or Firm*—McGlew and Tuttle

[57] ABSTRACT

A method for determining the alcohol content in the exhaling respiratory air using an alcohol measuring instrument and measuring the alcohol content when the exhaling air transmits the determined value of the alcohol concentration. This determined value of alcohol concentration occurs when the time variation related to the height of the alcohol signal is below a predetermined threshold value and the velocity of flow of the exhaling air is above a given value and is maintained without interruption for a given time. The apparatus includes an infrared measuring instrument which is connected into the respiratory air current and measures the alcohol concentration of the exhaling air. This value is applied to an indicator through a linear gate when an AND-gate is triggered by threshold comparators and a timing element activated by a threshold comparator.

8 Claims, 2 Drawing Figures

METHOD AND ARRANGEMENT FOR DETERMINING ALCOHOL CONTENT IN THE BREATH

FIELD AND BACKGROUND OF THE INVENTION

This invention relates in general to a method and apparatus for determining alcohol content in a person's breath and, in particular, to a new and useful method wherein the exhaling air is passed through an instrument which transmits the determined value of the alcohol concentration when the time variation related to the height of the alcohol signal is below a given threshold value, and to an apparatus for carrying out the method.

DESCRIPTION OF THE PRIOR ART

Methods and arrangements for measuring the alcohol content in respiratory air determine the true alcohol concentration, if only that part of the exhaust air which is in equilibrium, in the alveoli of the lungs, with the alcohol concentration of the blood is tested for its alcohol value. For this reason, the pendulum air from the oral and pharyngeal space and the mixed air must be measured separately from the alveolar air.

A known arrangement for detecting admixtures, particularly alcohol, in the exhaling air, uses a test tube for detecting alcohol wherein the exhaling air to be tested is blown over a mouthpiece through the test tube and into a bag. The bag ensures that the same amount of exhaling air is always used in all measurements. A nozzle arranged in the air passage determines the resistance to flow. Since, practically, only a certain exhaling pressure can be achieved with the human lung, the nozzle determines the velocity of the air through the test tube. The exhaling air blown into the bag over the test tube also contains, in addition to alveolar air, the pendulum air from the oral and pharyingeal space, which is not in exchange with the lungs. The measured alcohol content, therefore, is too low, corresponding to the volume portions of alveolar air. (German Pat. No. 1,052,630).

In the alcohol measuring instrument designed in accordance with another known method, both the $CO_2$ content and the alcohol content are measured in the exhaling air. Based on the idea that the $CO_2$ content is a measure for the exchange $O_2$ in the lungs, a high $O_2$-content must indicate breathing air from the lungs, hence, alveolar air. The measuring instrument measures the $CO_2$ content of the exhaled air, continuously at first, and after the given threshold value has been attained, according to this arrangement, it is 4.5% $CO_2$. The alcohol measuring unit is connected to measure the alcohol content in the breath. A generally applicable threshold value can therefore not be given. One test person will never attain the threshold value, while in another person, no alveolar air will yet be present, even though the threshold value has already been exceeded. In addition, an instrument from which the concentrations of two different gases must be determined is elaborate and sensitive. (U.S. Pat. No. 3,830,630).

Another known arrangement for determining the alcohol concentration in the breath measures the alcohol in the breathing air in a time period determined by a time control. This time period is determined by the course of a given time interval beginning within the exhaling period. The respiratory air throughout must not drop below a determined minimum throughput within this time interval, and the air must flow only in the exhaling direction. If these two conditions are not met, an error-detector determines the invalidity of the measurement. The time interval given ensures that the test person had already exhaled, at the time of measurement, the air from the oral cavity and trachea, and the measuring instrument then measures the alcohol concentration of the alveolar air. The end of the given time interval is determined by the time at which a minimum breathing air volume, preferably at least 80% of the entire breathing air volume, has been exhaled. An integrator can integrate, in time, the throughput of respiratory air during inhalation and exhalation, and determines therefrom the end of the time interval according to the minimum respiratory air volume. This embodiment is said to be independent of the body structure of the test person. The disadvantage of this device lies in its very complicated design since, for sanitary reasons, it must have two volume measuring units, one in the inhaling air passage and one in the exhaling air passage. In addition, the person tested cannot be expected to inhale through a channel through which the person tested before him has already exhaled. The agreement of the two volume measuring units cannot be achieved with simple parts. The same holds true for an absolutely necessary control. This method is not protected against measuring errors caused by a test person who is unwilling to take the test. In this case, the test person, by deliberate flat inhalation, can simulate a much too low breathing capacity. The minimum respiratory air volume, which is then established automatically, for example, at 80% of the total respiratory air volume, can then practically originate only from the oral cavity and the pharyngeal space. The alveolar air, which is determinant for an accurate measured value, is then not fully determined (German Pat. No. 2,428,352).

SUMMARY OF THE INVENTION

The present invention provides a simple and reliable method and measuring arrangement which ensures that only the alveolar air portion of the exhaling air is used for measuring alcohol content.

This problem is solved in a simple and reliable manner using the method of the invention in that an alcohol measuring instrument in the exhaling air transmits the determined value of the alcohol concentration when the time variation of S(t), related to the height of the alcohol signal S(t), is below a given threshold value, $$W \gtreqqless \frac{1}{S(t)} \cdot \frac{dS}{dt} \text{ and,}$$

the velocity of flow $v$ of the exhaling air is above a given value, and is maintained uninterrupted for a given time $t$.

The advantages achieved by this solution reside in the reliable determination of the alveolar air portion. This is accomplished by monitoring the time rise $dS/dt$ of the alcohol concentration. This time rise constantly decreases with the alveolar air portion following the exhaling air from the oral and pharyngeal space until it stops completely after the concentration plateau has been reached. When the rise related to the instantaneous concentration drops below the given threshold value W, only alveolar air is contained in the measuring channel of the alcohol measuring instrument. The monitoring of the rise in willing test persons would certainly suffice to determine reliably an alcohol concentration which is close to the value in the alveolar air. In practice, however, this willingness cannot always be achieved. For this reason, two additional conditions must be met, in addition to monitoring the rise, before a measuring value is indicated. The velocity of flow $v$ determined by a flow meter must be above a given value v-min, and must have been maintained for a given time in addition. The arrangement for the realization of the measuring method contains an infrared measuring instrument connected into the respiratory air current, which measures the alcohol concentration of the exhaling air and whose measured value appears on an indicating unit when an AND-gate, triggered simultaneously by a threshold comparator, an additional threshold comparator, and a timing element, triggers a linear gate.

The arrangement comprises a simple design which ensures simple handling with reliable results.

An infrared measuring instrument with a short response time <0.3s is used for the measurement. With this short response time, the monitoring of the rise can be controlled positively.

Accordingly, it is an object of the invention to provide a method for determining the alcohol content in exhalation air of a person using an alcohol measuring instrument which comprises passing the exhaling air through the instrument and measuring the alcohol content when the exhaling air transmits the determined value of the alcohol concentration and this occurs when the time variation related to the height of the alcohol signal is below a threshold value and the velocity of the flow of the exhaling air is above a given value and is maintained without interruption for a given time.

A further object of the invention is to provide an apparatus for measuring the alcohol content of respiratory air which includes an infrared measuring instrument connected into the respiratory air current and which measures the alcohol concentration of the exhaling air and which includes an indicator which is connected so that the measured value is applied to that indicator through a linear gate which is triggered by an AND-gate which is triggered by first and second threshold comparators and a timing element.

Another object of the invention is to provide an apparatus for determining the alcohol content in the breath of a person, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

DESCRIPTION OF THE PREFERRED EMBODIMENT

Figure 1:
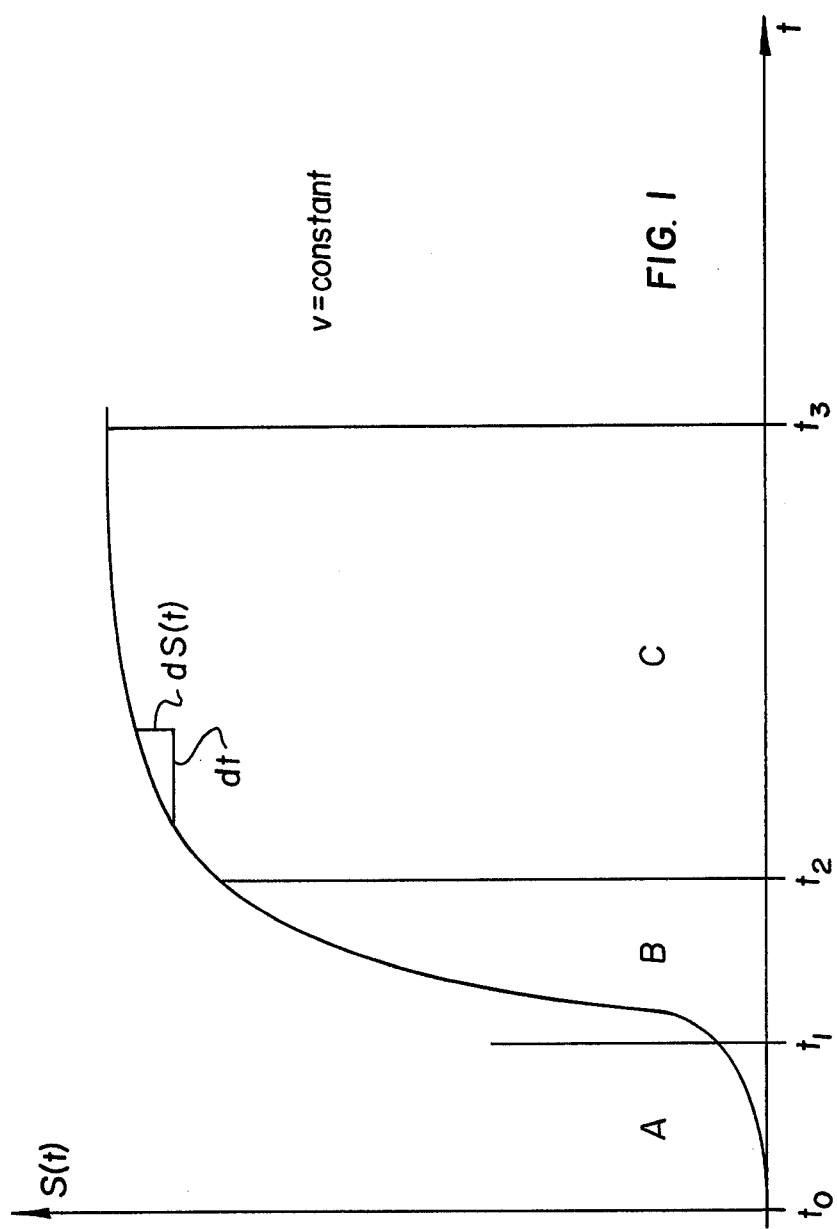
FIG. 1 is a curve showing the alcohol signal $S(t)$ against the time $t$.

Referring to FIG. 1, the time rise of the alcohol concentration in the respiratory air was plotted with the alcohol signal $S(t)$ as ordinate and the time $t$ as abscissa.

The curve shows three characteristic time sections A, B and C.

Section A, with the measuring time $t_0 - t_1$, shows a low alcohol concentration only at the end. Almost pure pendulum air is exhaled from the oral and pharyngeal space.

In Section B, with the measuring time $t_1 - t_2$, a steady rise of the alcohol concentration is observed. The pendulum air is mixed more and more with the alveolar air from the lungs.

Section C, with the time $t_2 - t_3$, shows almost no rise of the alcohol concentration and the curve moves on a plateau. Only alveolar is exhaled.

Figure 2:
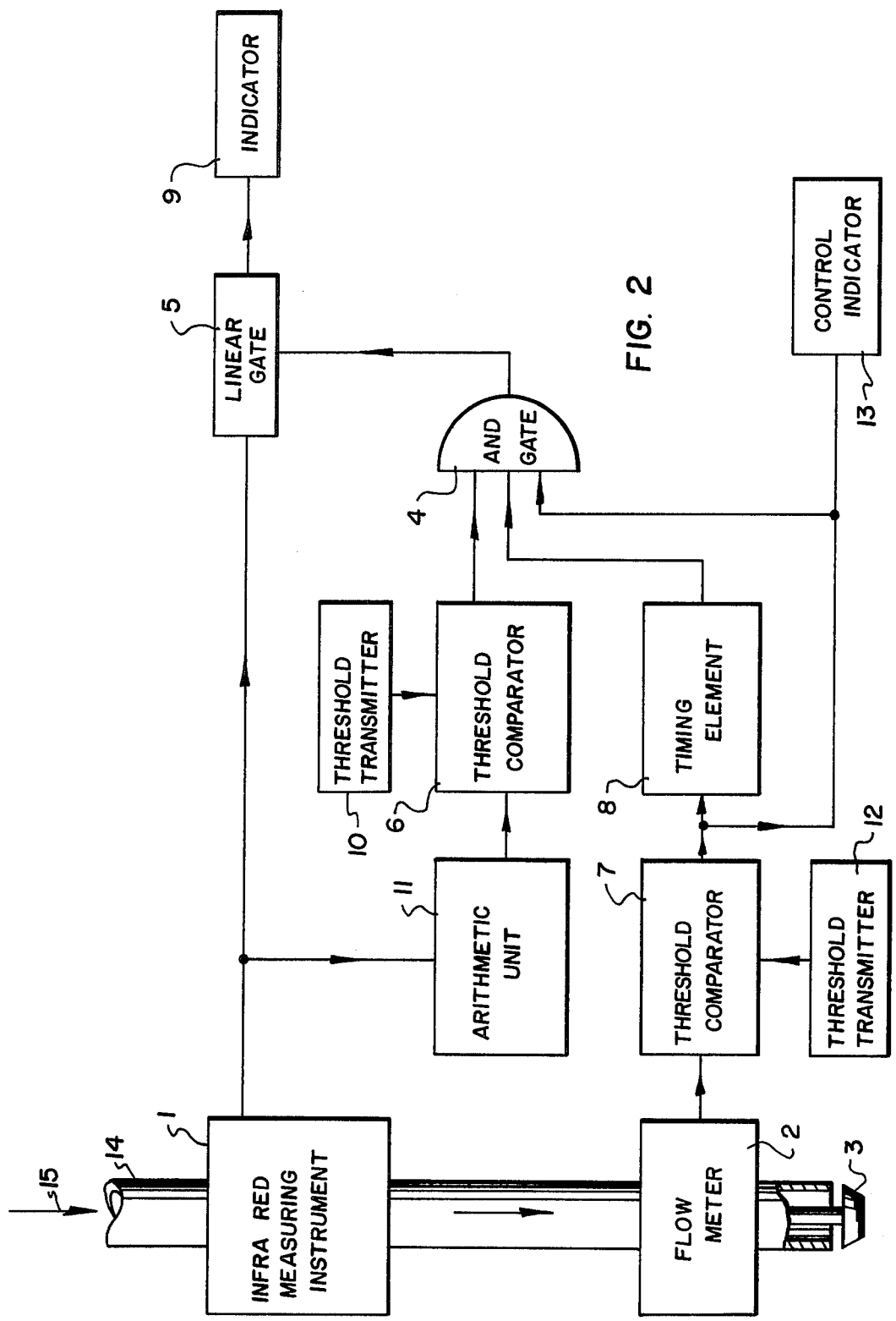
FIG. 2 is a block diagram of an apparatus for measuring the alcohol content of the respiratory air, constructed in accordance with the invention.

Section C is clearly recognized by the arrangement according to the invention, and as can be seen from FIG. 2. In the exhalation phase, it starts when the value $$G = \frac{1}{S(t)} \cdot \frac{dS}{dt}$$

of the rise monitoring drops below the threshold value W. There is then almost no rise of the alcohol value. In Section C, the infrared measuring device measures the alcohol concentration in the respiratory air which is in equilibrium with the blood. The infrared measuring instrument 1 corresponds to the state of the art. The volume of the optical measuring cell is about 50 ml, in adaptation to the physiological values, and can be filled with respiratory air in less than 0.3 sec. A photoconduction detector of PbSe comprises a radiation detector so that the rise time of the alcohol signal $S(t)$ can be determined with a time resolution of the instrument of 0.3 sec. for a 90% rise.

The infrared measuring instrument 1 for measuring alcohol is connected into the exhaling air current 14. The non-return valve 3 prevents a reversal of the exhaling air current 14 flowing in direction 15. A flow meter 2 which measures the velocity of flow $v$ is arranged behind the infrared measuring instrument 1. The AND-gate 4 delivers a control voltage to the linear gate 5, with which the alcohol signal $S(t)$ is transmitted from the infrared measuring instrument 1 over linear gate 5 to indicator 9.

A prerequisite for the control voltage from AND-gate 4 is that three conditions, $a$, $b$ and $c$ must be met:

a. The quantity G $$G = \frac{1}{S(t)} \cdot \frac{ds}{dt},$$

where G is determined in the arithmetic unit 11 connected to the output of the infrared measuring instrument 1, must have dropped below the threshold value W. Threshold value W is entered by threshold transmitter 10 and is compared in threshold comparator 6 with G. At $G \leq W$, a control signal is transmitted to the AND-gate 4.

b. The velocity of flow $v$ measured in flow meter 2 must be higher than the minimum velocity of flow $v_{min}$ entered by threshold transmitter 12. In this case, a threshold comparator 7 transmits a control signal to AND-gate 4.

c. Timing element 8 transmits a control signal to AND-gate 4 when the control signal has been applied to the output of threshold comparator 7 without interruption during a period determined by timing element 8.

The conditions a, b and c ensure that only alcohol signals S(t) from the alveolar air can be fed to indicator 9.

As the control signal of threshold comparator 7 drops to 0 during the measurement, when the velocity of flow $v$ has dropped below $v_{-min}$, the clock of timing element 8, and provided a control signal has been emitted at the output of timing element 8, also this control signal is reset to 0. The clock begins to run again when a control signal is again emitted by threshold comparator 7.

Control indicator 13 is connected between threshold comparator 7 and AND-gate 4. It lights up red when the velocity of flow $v < v_{-min}$ and green, when $v > v_{-min}$.

While a specific embodiment of the invention has been shown and described in detail to illustrate the application of the principles of the invention, it will be understood that the invention may be embodied otherwise without departing from such principles.

What is claimed is:

1. A method for determining the alcohol content, in exhalation air of a person, comprising the steps of passing the exhalation air through an alcohol measuring instrument, determining the alcohol concentration in the exhalation air, and providing an alcohol concentration output signal which increases to a plateau; measuring the flow velocity of the exhalation air passing through the measuring instrument; and, when the time variation of the alcohol concentration signal S(t) relative to the magnitude of the alcohol concentration signal is below a predetermined threshold value $$\frac{1}{S(t)} \cdot \frac{dS}{dt} \leq w$$

and when the flow velocity $v$ of the exhalation air is above a predetermined value and has been maintained thereabove for a predetermined time $t$, transmitting the determined value of the alcohol concentration signal to an indicator.

2. An apparatus for determining the alcohol content in exhalation air of a person, said apparatus comprising, in combination, an infrared alcohol measuring instrument; a flow meter for measuring the velocity of air; means for directing respiratory air in series through said infrared measuring instrument and said flow meter; said measuring instrument providing an alcohol concentration output signal which increases to a plateau; an alcohol concentration indicator; gating means connected between the output of said measuring instrument and the input of said indicators; an AND-gate having inputs and having an output connected to said gating means; a first threshold comparator connected to the output of said measuring instrument and to a first input of said AND-gate; a second threshold comparator connected to the output of said flow meter and to a second input of said AND-gate; and a timing element connected to the output of said second threshold comparator and to a third input of said AND-gate; said AND-gate, responsive to simultaneous triggering of its three inputs, providing an output signal to said gating means to trigger said gating means to connect the output of said measuring instrument to said indicator; said first threshold comparator supplying an input signal to said AND-gate when the time variation of the alcohol concentration signal, relative to the magnitude of the alcohol concentration signal, is below a predetermined threshold value; said second threshold comparator providing a signal to said second input of said AND-gate when the velocity of the exhalation air is above a predetermined value; said timing element being activated by said second threshold comparator and providing a signal to said third input of said AND-gate when the velocity of the exhalation air has been maintained above said predetermined value for a predetermined time.

3. An apparatus, according to claim 2, wherein said infrared measuring instrument has a response time of less than 0.3 sec.

4. An apparatus, according to claim 2, including a first threshold transmitter connected to said first threshold comparator and transmitting to said first threshold comparator a threshold signal W; an arithmetic unit connected to the output of said measuring instrument and to an input of said first threshold comparator and supplying thereto a signal G representing the time variation of the alcohol concentration signal S(t) relative to the magnitude of the alcohol concentration signal; said first threshold comparator supplying a signal to said first input of said AND-gate when $$G = \frac{1}{S(t)} \cdot \frac{dS}{dt} \leq W.$$

5. An apparatus, according to claim 2, in which said flow meter provides, to said second threshold comparator, a signal $v$ corresponding to the actual flow velocity of the exhalation air through said flow meter; a second threshold transmitter connected through an input of said second threshold comparator and supplying to said second threshold comparator a signal $v_{min}$; said second threshold comparator supplying its output signal to said second input of said AND-gate and to said timing element when $v$ is higher than $v_{min}$.

6. An apparatus, according to claim 5, in which said timing element is activated responsive to the output signal of said second threshold comparator and transmits an output signal to said third input of said AND-gate responsive to the output signal from said second comparator continuing, without interruption, for a predetermined time interval.

7. An apparatus, according to claim 5, including a control indicator connected to the output of said second threshold comparator and providing a first signal when $v$ is less than $v_{min}$ and a second signal when $v$ is greater than $v_{min}$.

8. An apparatus, according to claim 2, in which said means for directing respiratory air through said measuring instrument and said flow meter includes a non-return valve preventing reverse flow to said measuring instrument and said flow meter responsive to the person inhaling air.

* * * * *